(12) United States Patent
Groop et al.

(10) Patent No.: US 10,967,163 B1
(45) Date of Patent: *Apr. 6, 2021

(54) STERILE APPLICATOR ASSEMBLY WITH HOLLOW MICRONEEDLE ARRAY

(71) Applicant: Esthetic Education LLC, Scottsdale, AZ (US)

(72) Inventors: Kristin Groop, Scottsdale, AZ (US); Lawrence Groop, Scottsdale, AZ (US)

(73) Assignee: Esthetic Education LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/989,874

(22) Filed: Aug. 10, 2020

(51) Int. Cl.
   *A61M 35/00* (2006.01)
   *A61M 37/00* (2006.01)

(52) U.S. Cl.
   CPC ...... *A61M 35/003* (2013.01); *A61M 37/0015* (2013.01); *A61M 2210/04* (2013.01)

(58) Field of Classification Search
   CPC ............ A61M 35/003; A61M 37/0015; A61M 2210/04; A61H 7/003; A61H 2201/105; B65D 47/42; A61K 9/0021
   See application file for complete search history.

(56) References Cited

U.S. PATENT DOCUMENTS

| | | | | |
|---|---|---|---|---|
| 1,467,242 | A * | 9/1923 | Elstein | A61M 3/0279 604/279 |
| 6,238,120 | B1 * | 5/2001 | Mark | A45D 19/02 401/134 |
| 6,439,241 | B2 * | 8/2002 | Berke | A45D 34/04 132/200 |
| 8,857,004 | B1 * | 10/2014 | Luis | A46B 15/0069 15/167.1 |
| 8,938,841 | B1 * | 1/2015 | Ramirez | A46B 9/045 15/106 |
| 10,434,294 | B2 * | 10/2019 | Groop | A61M 35/003 |
| 2009/0234322 | A1 * | 9/2009 | Fischer | A61M 5/346 604/512 |
| 2016/0279342 | A1 * | 9/2016 | Park | A61M 5/3243 |
| 2019/0151637 | A1 * | 5/2019 | Groop | A61M 35/003 |

FOREIGN PATENT DOCUMENTS

| | | |
|---|---|---|
| CN | 102462875 | 5/2012 |
| CN | 103212144 | 7/2013 |
| KR | 101675333 | 11/2016 |
| KR | 101705317 | 2/2017 |

* cited by examiner

*Primary Examiner* — Ariana Zimbouski
*Assistant Examiner* — Gabriella E Burnette
(74) *Attorney, Agent, or Firm* — Joseph W Mott; Hartman Titus PLC

(57) ABSTRACT

A soft tip applicator attaches to a syringe for spreading expressed liquid from the syringe onto a surface, such as skin. A detachable hollow microneedle assembly supports transdermal injection of syringe contents.

9 Claims, 6 Drawing Sheets

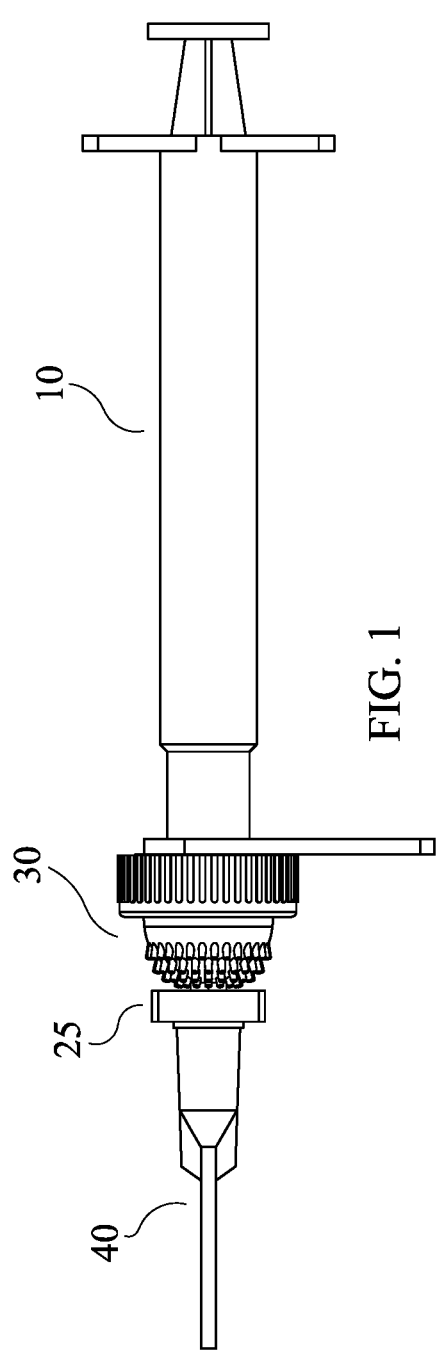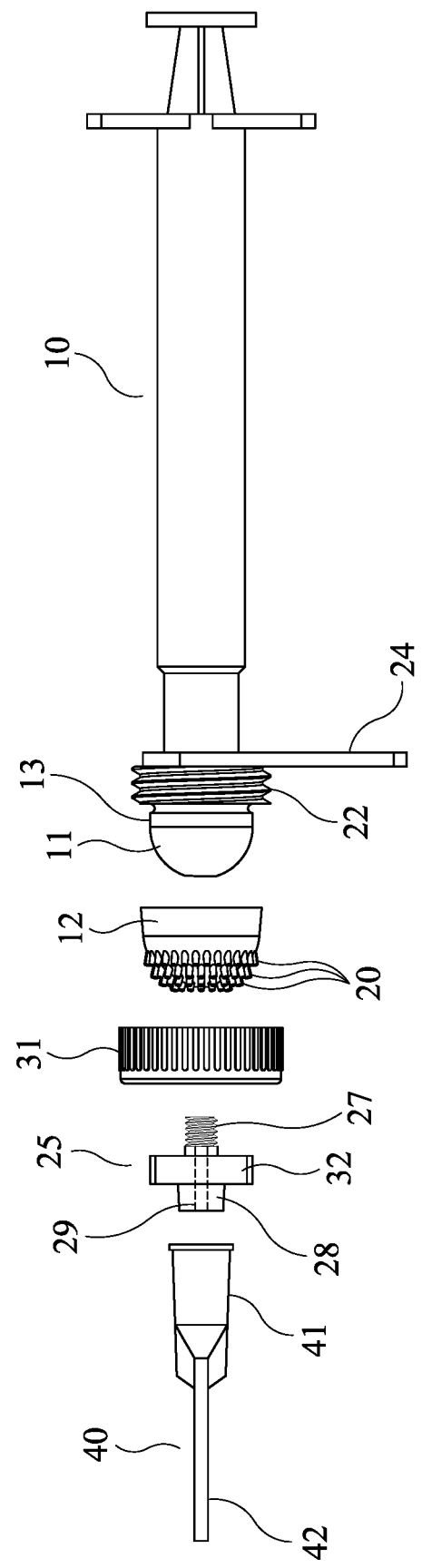
FIG. 1
FIG. 2

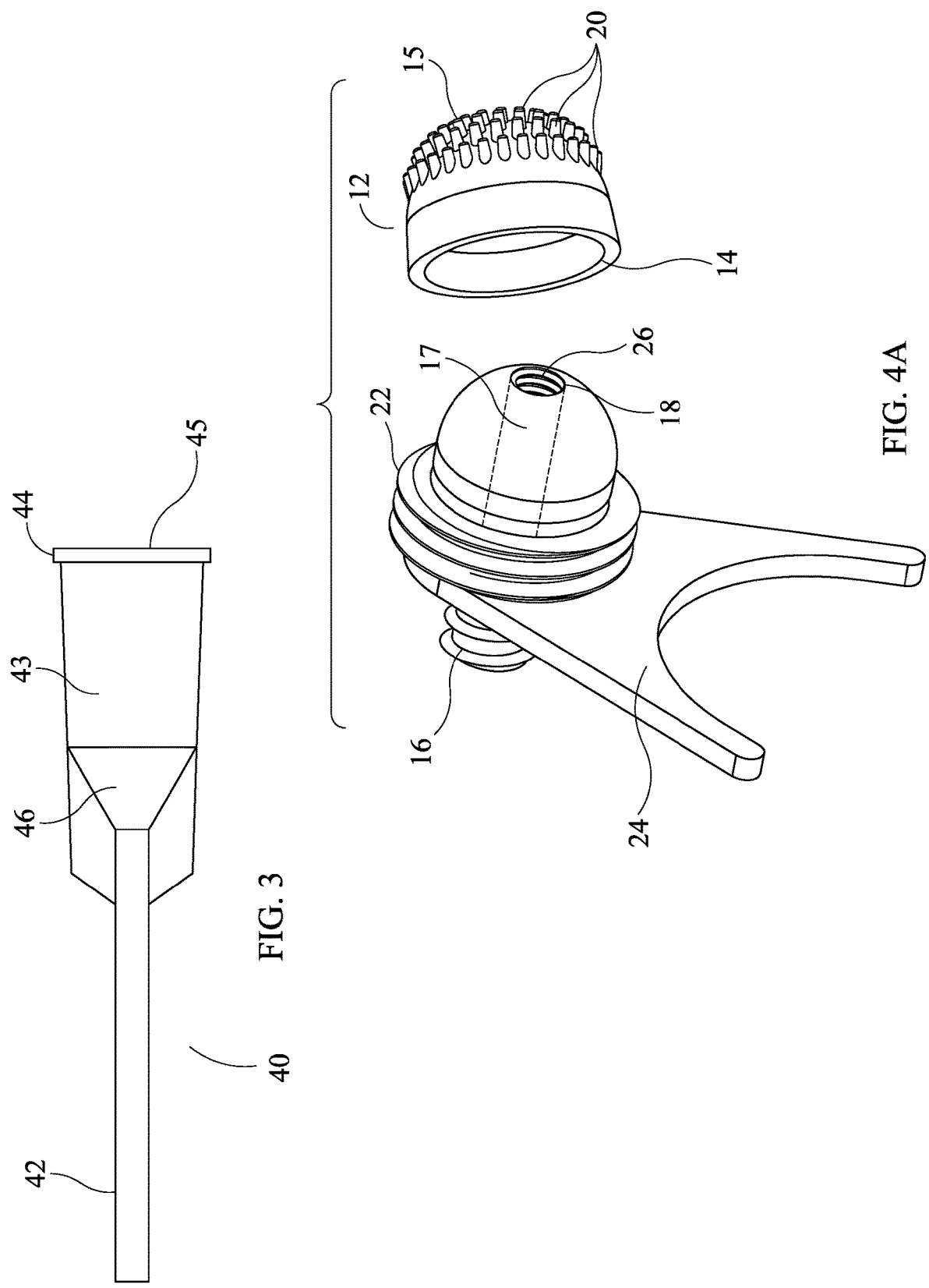

STERILE APPLICATOR ASSEMBLY WITH HOLLOW MICRONEEDLE ARRAY

TECHNICAL FIELD OF THE INVENTION

The disclosed device relates to a spring loaded solution injector, and more particularly, to a spring loaded manual solution injection system using a multineedle array all of which connects to a standard luer syringe for quickly and easily injecting a solution into the skin at operator selected depths.

BACKGROUND OF THE INVENTION

In 1952, French doctor Michel Pistor developed the treatment method known as mesotherapy that is now widely practiced worldwide.

The treatment method involves injecting a small amount of the therapeutic agent into the skin layer and the subcutaneous layer using a special motorized injection device and a microinjection needle or needle array.

Mesotherapy has been used in the treatment of acute and chronic pain, partial obesity, and to improve the appearance of skin wrinkles and skin aging. Its effect is immediate, there is only mild discomfort in the treatment, and there are few side effects.

In comparison to mesotherapy devices, injecting medicaments into the skin with a single needle connected to a manual thumb pressure plunger type syringe takes much longer, is more painful and quickly results in operator fatigue.

In current mesotherapy devices, a meso gun or an injection gun is used as a means for automatically injecting a chemical liquid. However, it is necessary to change needle array cartridges to adjust the depth of penetration into the skin as each cartridge has needles with a fixed length/depth in these meso gun devices.

An adaptation of a syringe-connectable applicator for skin surface treatments, as shown in U.S. patent Ser. No. 10/441, 763, may be effective and useful in administration of mesotherapy treatments without a complex injection gun.

The applicator is combined with a hollow microneedle injection apparatus to provide percutaneous delivery of bioactive agents, such as medicines or cosmetics, to the skin. The applicator is detachable from the microneedle injection apparatus and allows the user to apply treatment liquid coincident with hollow microneedle injection.

The entire assembly of cannula, connector, applicator, and its connection to the syringe must have a continuous lumen so liquid can be expressed from the syringe, into the injection apparatus, and out through the lumens of needles in the array. As most syringes incorporate a standard luer lock, an embodiment of the applicator incorporates a standard luer lock connection.

SUMMARY OF THE DISCLOSURE

An applicator assembly is provided that attaches to a syringe, which may be a standard barrel syringe, with a lumen that runs from the syringe to an exit aperture in the tip of a soft polymer applicator. In an embodiment, a nub attaches to the syringe and a soft silicone applicator stretches over the nub. A connector interfaces between the nub and a cannula hub with attached cannula. The assembly allows fluid to be drawn through the cannula into the syringe and then, with the cannula removed, expressed from the syringe. A microneedle platform with a liquid distribution chamber and hollow microneedles may be attached to the nub, allowing mesotherapy treatment directly from the syringe.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIG. 1 is a side view of an embodiment of the applicator assembly attached to a barrel syringe.

FIG. 2 is an exploded view of the assembly of FIG. 1.

FIG. 3 is a detailed view of an embodiment of a cannula hub for use with the applicator assembly.

FIG. 4A is an exploded view showing a nub and its associated soft applicator cover in an embodiment of the invention.

DETAILED DESCRIPTION OF EXAMPLE EMBODIMENTS

Figure 4C:
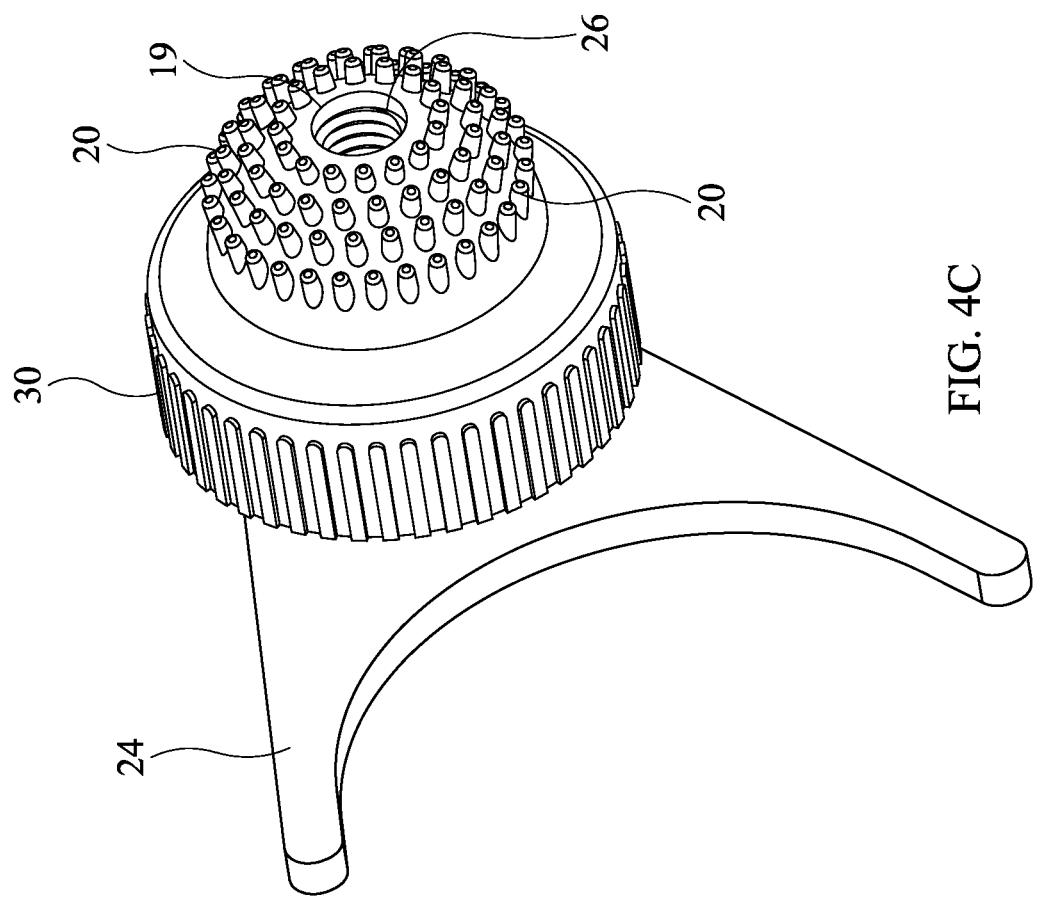
FIG. 4C shows the nub and applicator of FIGS. 4A and 4B with a securing collar attached.

An embodiment of the applicator assembly is shown in FIGS. 1 and 2. An applicator assembly 30 attaches to a barrel syringe 10, which may be a standard luer lock syringe. A connector 25 removably attaches a cannula 40, which may be a common hub-and-cannula unit, to the applicator 30.

Applicator 30 comprises an attachment nub 11 that fits into the syringe 10 and a soft applicator cover 12 that fits tightly over the nub 11 Connection of the attachment nub 11 to the syringe 10 may be by luer lock, in which the nub has a male luer configuration matching the female luer threads on the syringe. Other connections may be used, such as threading or a friction fit. To aid in stabilization, nub 11 may have a 360 degree groove 13 that matches to a 360 degree inward peripheral ridge 14 in the applicator cover 12.

The soft polymer applicator itself is a cover 12 with a rounded tip 15 that fits tightly over a hemispheric nub 11. It may be made of medical grade thermoplastic resin or medical grade silicone. In one embodiment it incorporates a plurality of soft filament projections, or tendrils 20, about ³⁄₁₆ inch (4.75 mm) long and 0.8 mm in diameter radiating outward. These "koosh" extensions allow effective dispersion of a viscous liquid while remaining comfortable to the skin. Different filament characteristics may be employed depending on the specific use for the applicator. For example, in the event of hair restoration, a modified silicone membrane with longer, stiffer extensions may provide a means of reducing the resistance of the hair as the applicator is being moved to distribute the liquid.

Figure 4B:
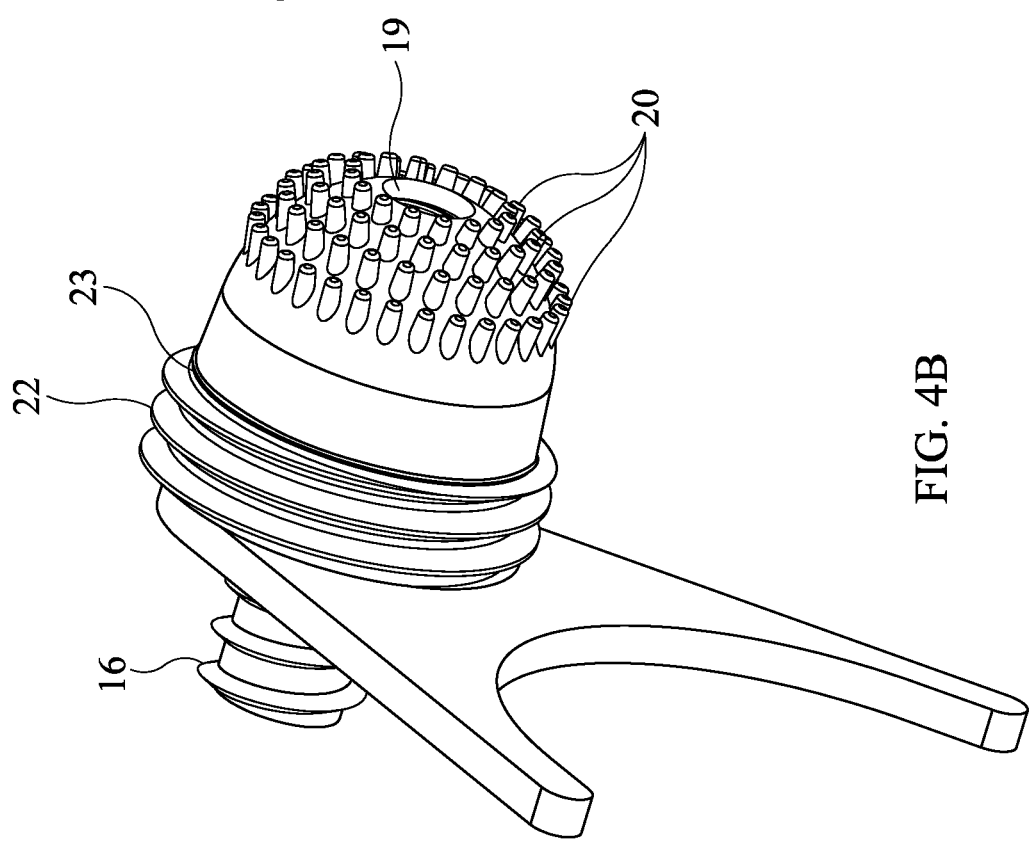
FIG. 4B shows a nub with a soft applicator cover attached.

The nub 11 that supports a soft tip covering 12 may be any hard material, and is preferably a plastic, such as polypropylene. See FIGS. 4A-4C. As noted, the nub 11 engages the syringe in some manner. In an embodiment, a proximal cylindrical extension of the nub 11 has male luer threads 16 that fit female luer threads (not shown) on the syringe. A tunnel or lumen 17 extends through the nub, terminating in an aperture 18 for liquid flow. The applicator cover has a corresponding aperture 19. In an embodiment, a central cylindrical segment of the nub may include external threads 22 that engage threads in a securing collar 31 that helps hold the applicator cover in place. To better implement this feature, an external peripheral ridge 23 may be added to the above mentioned internal peripheral ridge in the applicator cover. An optional stand 24, which may be plastic, snaps onto the nub 11 to keep the tip off the table surface.

The distal portion of the nub is configured to optionally engage a cannula connector 25. In an embodiment, the connector may be a two way male threaded cross shaped fitting 25, with extension 27 adapted to engage female connector threads 26 on the nub 11, and extension 28, adapted to engage a cannula hub 41. A lumen 29 through the connector permits liquid to pass between the nub and the cannula. Other connection means, such as friction fit to the nub, or threaded fit to the cannula hub, may be employed. Some cannula hubs have external male luer lock threads, and an appropriate configuration might incorporate corresponding female threads on the distal extension of the connector.

The cross bar 32 of the connector 25 allows the user to easily twist the connector, unscrewing it and separating the applicator tip from the cannula. The cannula connector is also sterile and removable.

As noted, a cannula assembly 40, comprising a cannula 42 and cannula hub 41 are attached to the distal end of the assembly. Cannula hubs of various types are known in the industry and provide a funnel-like transition from a wider aperture, such as in a syringe, to the narrow lumen of a small, usually metal, cannula. Most cannula hubs are hard plastic, but other materials, such as aluminum may be suitable. An embodiment of a cannula hub is shown in FIG. 3. The proximal end is a cylindrical chamber 43 that tapers toward its distal end. An upper flange 44 surrounds the opening and there may be male luer threads around the outside. The inner surface 45 of the chamber is smooth. The distal end 46 of the hub tapers more severely than the upper chamber, resulting in an opening that firmly engages the cannula 42 The most common cannula sizes for skin and blood applications are between 20 gauge and 12 gauge.

Figure 5:
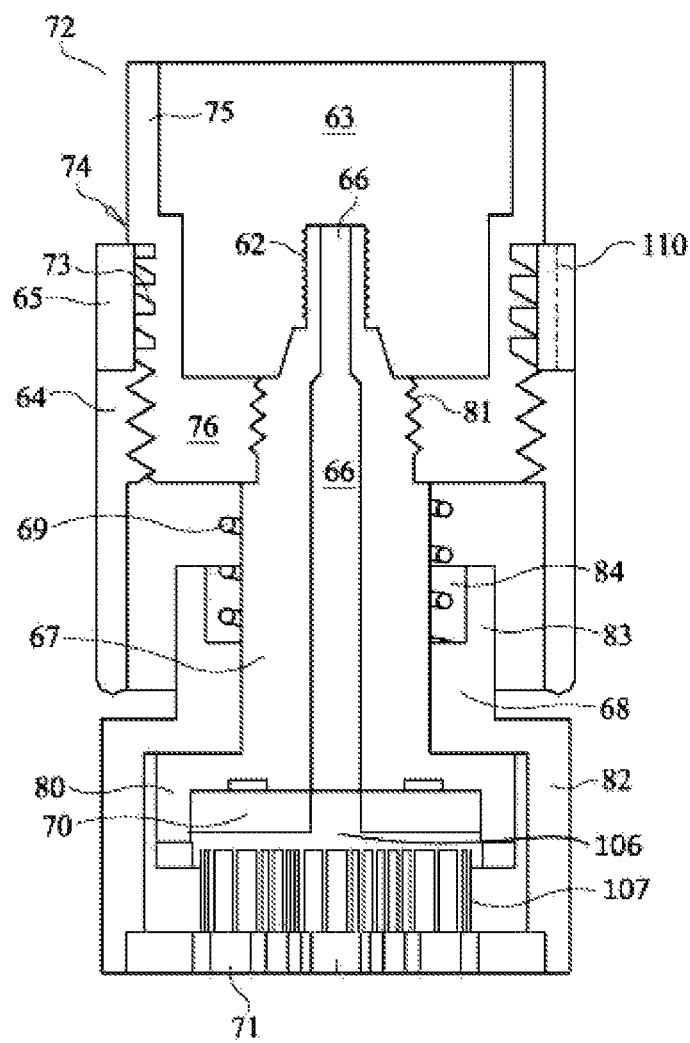
FIG. 5 shows an assembled view of an embodiment of a microneedle injection apparatus.

In operating the device, cannula 42 may be used to draw liquid into syringe 10 and may then be disengaged by detaching connector 25 thereby uncovering and allowing the applicator 30 to dock via screw threads into the hollow microneedle injection apparatus (shown in FIG. 5).

Figure 6:
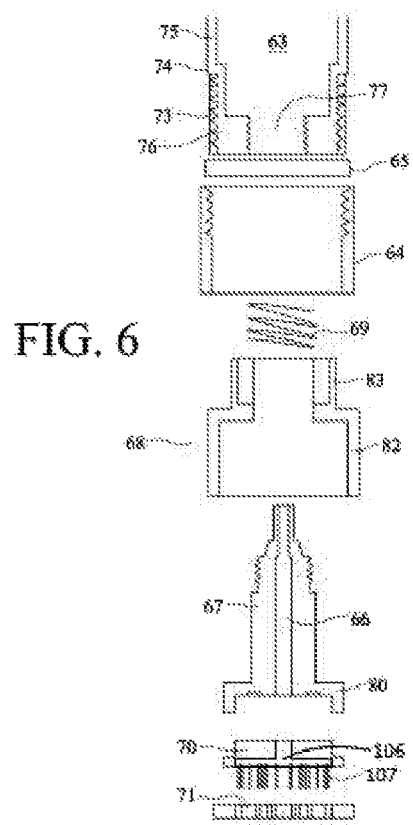
FIG. 6 shows an exploded view of the microneedle injection apparatus of FIG. 5.
Figure 7:
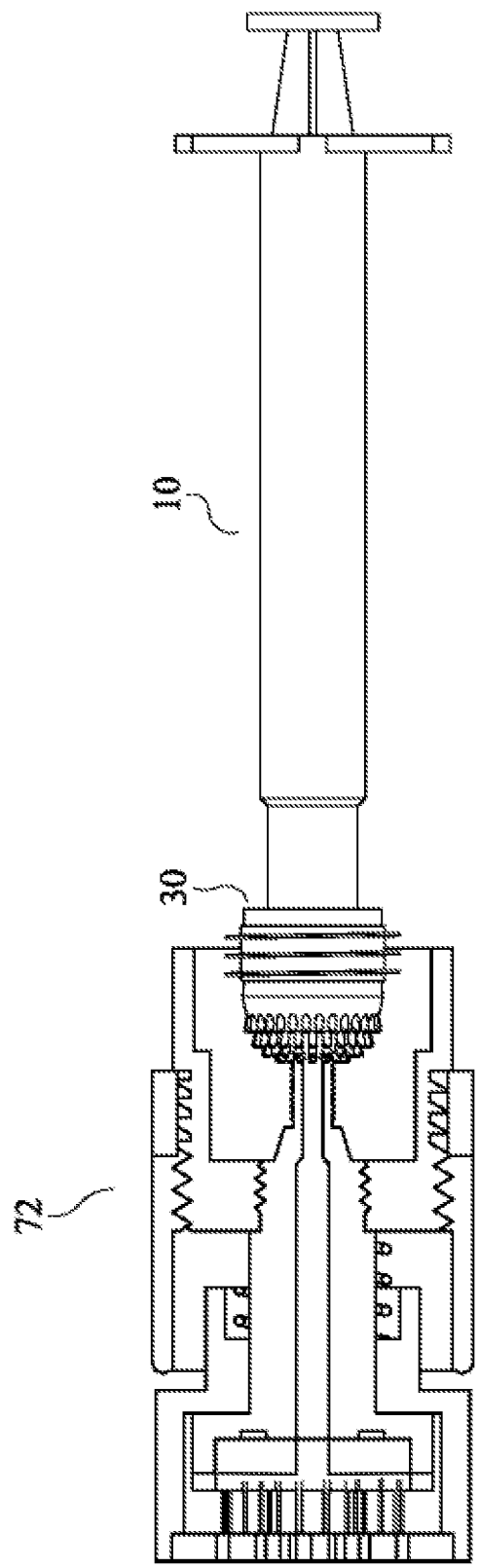
FIG. 7 shows an embodiment of a microneedle injection apparatus attached to an applicator assembly.

FIGS. 5 and 6 show how the applicator 30 system connects to the hollow microneedling apparatus 72 and provides continuous liquid communication from the syringe to a plurality of hollow microneedles. This hollow microneedle apparatus 72 comprises threaded applicator attachment extension 62, threaded upper cylinder body 63, distal threaded depth control adjustment cylinder 64, proximal unthreaded removable depth control cylinder 65 with vertical score line 110, central lumen 66, threaded array plate body 67, lower cylinder body 68, spring 69, needle array plate 70 with central lumen, liquid distribution chamber 106, hollow hypodermic needles 107, and safety plate 71. In the description of FIGS. 5 and 6, the upper side of the drawings will be referred to as proximal and the lower side as distal because the needle array plate 70 will be distal to the applicator and syringe when the stamping apparatus is attached to the soft applicator and syringe.

Threaded upper cylinder body 63 may comprise a cylinder that has external threads 73 around its lower, or distal, half. The outer diameter of the unthreaded proximal portion 74 is slightly wider than the threaded outer diameter and the cylinder wall thickness 75 in the unthreaded proximal portion may be slightly thinner than that of the threaded portion, to allow a slightly larger proximal opening in the cylinder. About one half of the externally threaded portion 73 comprises a closed bottom 76 with an internally threaded aperture 77.

Array plate holder 67 may comprise a solid, smooth sided cylinder with a central lumen 66. The inside diameter of the distal end 80 is expanded to accommodate a needle array plate 70, to which a plurality of hollow hypodermic microneedles 107 are attached and the proximal open ends terminate inside liquid distribution chamber 106. The proximal end of array plate holder 67 comprises two threaded portions. External threads 62 correspond to the female threads 26 on nub 11 of the applicator, as discussed below. Distal to the external threads 62, the plate holder body 67 widens to accommodate external threads 81, which correspond to the internal threads of aperture 77 of the threaded upper cylinder body 63. Lumen 66 extends through the array plate holder 67 and continues through the array plate 70 and then terminates into liquid distribution chamber 106 which allows the liquid to be expressed through hollow hypodermic microneedles 107 and into the skin.

Supporting lower cylinder body 68 comprises a distal portion having an outside diameter approximately the same as the outside diameter of threaded upper cylinder body 63 and an inside diameter that slidably retains distal end 80 of array plate holder 67. Proximal portion 83 of lower cylinder body 68 has an inside diameter that slidably engages the smooth central portion of array plate holder 67. Safety plate 71, with apertures permitting passage of microneedles 90 is affixed to the distal end of lower cylinder body 68. A circular groove 84 in the proximal end 83 of lower cylinder body 68 accommodates a surrounding spring 69.

Hollow microneedle penetration depth control is provided via a proximal unthreaded removable depth control cylinder 65 and a distal threaded depth control adjustment cylinder 64 with internal threads corresponding to the external threads 73 on threaded upper body cylinder 63.

To assemble the apparatus 72, proximal unthreaded removable depth control cylinder 65 is slid onto threaded upper cylinder body 63 until it stops at the base of the screw threads 74 where the upper cylinder body widens to form a stop. Distal threaded depth control adjustment cylinder 64 is then screwed onto threaded upper cylinder body 63 until it contacts and is stopped by proximal unthreaded removable depth control cylinder 65. Needle array plate with central lumen 70 is seated and glued into the wide, distal end of threaded array plate body 67. Threaded array plate body 67 is placed inside the distal end of lower cylinder body 68 until the distal proximal shoulder of threaded array plate body 67 is contacted by the distal shoulder of lower cylinder body 68. Spring 69 is placed around threaded array plate body 67 and slid distally into groove 84. Threaded array plate body 67 is then screwed into threaded upper cylinder body 63 compressing spring 69 slightly, loading it. Glue may be used to secure threaded array plate body 67 onto the screw threads of threaded upper cylinder body 63. Finally, safety plate with central lumen 71 is attached inside the shoulder rest at the distal end of lower cylinder body 68.

The applicator apparatus 30 can be connected to the microneedle stamping apparatus 72 by unscrewing cannula connector 25 from the female connector threads 26 on the nub 11. Once the cannula connector 25 is removed, the two apparatuses are connected by threading the array plate holder's 67 proximal threads 62 onto the female connector threads 26 until the soft applicator cover 12 is firmly seated into the cavity of threaded upper cylinder body 63. See FIG.

7. This process connects and seals the connection between aperture 52, which is contiguous with internal cavity 51, and the central lumen through threaded plate body 66.

Once assembled the operator places the distal surface of safety plate 71 against the skin and presses down on syringe 10. Depending on the depth set via threaded depth control adjustment cylinder 64, the downward pressure will move threaded lower cylinder body 63, threaded depth control adjustment cylinder 64, proximal removable depth control cylinder 65, threaded array plate body 67, and needle array plate 70, downwards forcing the needles 107 past safety plate 71 and into the skin. The downward motion will be stopped when the distal end of threaded depth control adjustment cylinder 64 contacts the proximal shoulder of support cylinder body 68. This downward motion compresses spring 69.

The operator may choose to express the liquid inside syringe 10 into the skin by pressing down on the syringe plunger which forces liquid through central lumen 66, into liquid distribution chamber 106, then into hollow hypodermic needles 107, and then into skin at prescribed depth.

When the operator stops downward motion and begins to pull up to withdraw the needles, the withdrawal of the needles from the skin is assisted by spring 69 uncompressing and assisting the upward motion of threaded upper cylinder body 63 and threaded array plate body 67, withdrawing the needles 107 past safety plate 71.

The depth of penetration may be controlled by rotating distal threaded depth control adjustment cylinder 64 distally or proximally on threaded upper cylinder body 63. There may be a depth indicator arrow marked (or etched) onto the outside of distal threaded depth control adjustment cylinder 64 and depth setting markings, representing depth of penetration in millimeters, marked (or etched) on the outside of lower cylinder body 68. The operator can choose the depth of penetration by aligning the depth indicator arrow with the chosen depth marking.

The proximal unthreaded removable depth control cylinder 65 with vertical score line 110 restricts needle penetration to a maximum depth of 0.3 mm when turning distal threaded depth control adjustment cylinder 64. In most cases, this depth restriction corresponds to the maximum depth in the epidermis, as is required for certain practitioners in certain jurisdictions. Proximal unthreaded removable depth control cylinder 65 with vertical score line 110 may be removed by placing a thin, flat edge, such as a flat head screwdriver blade, into the vertical score line 110 and twisting until the ring is broken and can be removed. Once removed, distal threaded depth control adjustment cylinder 64 can move the entire range allowing a deeper penetration setting than 0.3 mm.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

What is claimed is:

1. An applicator for spreading liquid from a syringe onto a surface, comprising
   a hemispheric nub with a central lumen, the nub being removably attachable to the syringe;
   a soft polymer applicator cover over the nub, having a plurality of flexible tendrils and an aperture aligned with the lumen;
   a microneedling platform comprising a plurality of hollow microneedles and a liquid distribution chamber in liquid communication with the lumen;
   a connector for removably attaching the microneedling platform to the nub;
   an upper cylinder body enveloping the nub and connector; and a lower cylinder body enveloping the microneedling platform.

2. The applicator of claim 1, wherein the microneedling platform is configured to move reciprocally within the lower cylinder body and a spring to assist withdrawal of the platform from an extended position.

3. The applicator of claim 2, further including a safety plate attached to the lower cylinder body, having apertures that allow reciprocal passage of the microneedles.

4. The applicator of claim 3, further including a depth controller for adjustably regulating the distance that the microneedles can extend beyond the safety plate.

5. The applicator of claim 4, wherein the depth controller comprises an adjustment cylinder positioned generally between the upper cylinder body and the lower cylinder body, with threading to connect the adjustment cylinder to the upper cylinder body.

6. The applicator of claim 5, further comprising a removable depth control cylinder positioned adjacent to and above the adjustment cylinder.

7. An applicator for spreading liquid from a syringe onto a surface, comprising
   a hemispheric nub with a central lumen, the nub being removably attachable to the syringe;
   a soft polymer applicator cover over the nub, having a plurality of flexible tendrils and an aperture aligned with the lumen of the nub;
   a microneedling platform comprising a plurality of hollow microneedles and a liquid distribution chamber in liquid communication with the lumen;
   a connector for removably attaching the microneedling platform to the nub;
   an upper cylinder body enveloping the nub and connector, and a lower cylinder body enveloping the microneedling platform;
   a safety plate attached to the lower cylinder body, having apertures that allow reciprocal passage of the microneedles;
   a spring to assist withdrawal of the platform from an extended position;
   and a depth controller for adjustably regulating the distance that the microneedles can extend beyond the safety plate.

8. The applicator of claim 7 wherein the depth controller comprises an adjustment cylinder positioned generally between the upper cylinder body and the lower cylinder body, with threading to connect the adjustment cylinder to the upper cylinder body, and a removable depth control cylinder positioned adjacent to and above the adjustment cylinder.

9. The applicator of claim 8, further including a syringe.

* * * * *